United States Patent [19]

Khan et al.

[11] Patent Number: 5,124,249
[45] Date of Patent: Jun. 23, 1992

[54] METHOD FOR EVALUATING PROTECTION TO BEE VENOM

[76] Inventors: Rashid H. Khan, 67 Village Drive, Apt. 907, Kingston, Ontario, K7K 6K7, Canada; Myron R. Szewczuk, 378 Renda St., Kingston, Ontario, K7M 5Y1, Canada; James H. Day, 827 Wartman Ave., Kingston, Ontario, K7M 4M3, Canada

[21] Appl. No.: 442,910

[22] Filed: Nov. 28, 1989

[51] Int. Cl.⁵ .................. G01N 33/53; G01N 33/542; G01N 33/577
[52] U.S. Cl. .................. 435/7.5; 435/7.9; 435/965
[58] Field of Search .......... 435/7.1, 7.5, 7.9, 7.92, 435/7.94, 965; 436/518, 540, 547, 548, 811

[56] References Cited

U.S. PATENT DOCUMENTS 4,536,479  8/1985  Vander-Mallie .................... 436/537

OTHER PUBLICATIONS

Saxon et al., J. Clin. Invest. 73:342-348, 1984.
Bose et al., J. Immunol. 135:2474-2478, 1984.
Towbin et al., J. Immunol. Methods 72:313-340, 1984.
Sigma Immunochemicals, 1989 catalog, St. Louis, Mo., Item A5026.
Sevier et al., Clin. Chem. 27:1797-1806, 1981.
Maggio, E. T., Ed., Enzyme Immunoassay, CRC Press, Boca Raton, Fla., 1980, pp. 167-179.

*Primary Examiner*—Esther L. Kepplinger
*Assistant Examiner*—Donna C. Wortman

[57] ABSTRACT

Venom immunotherapy is a highly effective treatment for bee sting sensitive individuals. Treated individuals and those naturally exposed to repeated bee stings, such as beekeepers have been shown to develop anti bee venom anti-idiotypic antibodies. These antibodies can be isolated, monoclonal anti-bee venom antibodies can be generated and used in a diagnostic kit to evaluate whether or not an affected individual has developed effective immunity, and to evaluate an individual's risk of sensitivity.

5 Claims, 5 Drawing Sheets

PRE-IMMUNOTHERAPY
POST-IMMUNOTHERAPY
POST-IMMUNOTHERAPY (5207)
(8186)

METHOD FOR EVALUATING PROTECTION TO BEE VENOM

FIELD OF INVENTION

This invention relates to an immunological method for identifying patients sensitive to bee stings, and more particularly to a method for determining a patient's protection against bee venom, and to the isolation of anti-idiotypic antibodies against anti-bee venom.

BACKGROUND OF INVENTION

Allergic reactions to hymenoptera stings (bees, bumble bees, yellow jackets, wasps, hornets and the like) are often serious and can be life threatening. It is estimated that 40-50 persons die each year in the United States from insect sting allergy. In a survey of a large adult population in the Baltimore, Md., area, 4% of the population reported a history of systemic sting reactions, while 20% of family members of bee keepers were reported to have systemic reactions. Estimates of hymenoptera sting sensitivity in a general population by history alone ranged between 0.4 and 0.8% of the population. In another study of fatalities due to insect stings, only two of nine fatalities had a positive history of generalized reaction to insect stings. This not only demonstrates the high incidence of sting sensitivity especially in high risk groups and the potential fatalities of such stings but also indicates the importance of predicting serious reactions in high risk individuals. Protection may be natural or induced as a result of immunotherapy or multiple stings over a long period of time such as observed in beekeepers.

Immunotherapy (IT) has been shown to be beneficial for a variety of allergens, particularly for insect sting sensitivity.

Immunotherapy for bee sting sensitivity involves injection of gradually increasing amounts of bee venom (BV) at regular intervals, starting with a minute amount. The regime is empiric but usually when the individual is able to tolerate 50 μg of venom (average amount of venom in a single bee sting) with no systemic reaction, the dose may be increased up to a total dose of 100 μg venom per month and IT maintained at this dose, until a sting without a reaction occurs. Discontinuation of ITA after 5 years if no reaction occurs during this time has been suggested to provide protection for at least two years after cessation of IT. Protection, however, is a complex and dynamic process and may decline upon cessation of immunotherapy. The mechanism(s) by which immunotherapy protects is not completely understood. It has been shown that immunotherapy results in reduction of venom specific IgE and the production of venom specific 'blocking' IgG antibodies. These antibodies are closely associated with protection presumably by competing for venom antigens with mast cell bound IgE antibodies and thus preventing histamine release.

Cellular events leading to the increased synthesis and suppression of IgE antibodies have also been described. T cells can release lymphokines which can influence B cells and macrophages in many different ways. T helper and suppressor cells can have profound influence on the production and suppression of IgE synthesis. The influence of IT on the regulatory role of these cells on IgE synthesis is currently under investigation in a number of laboratories. Various IgE specific suppressive and enhancing factors have recently been described. These factors have molecular weights which range from 10,000 to 150,000. In addition to IgE antibodies which are known as the major class of antibodies responsible for the release of histamine and other mediators from sensitized mast cells and basophils, IgG4 antibodies have also been shown to sensitize effector cells in animals and cause mediator release. These antibodies have been found with increased frequency to food antigens in asthmatic patients compared to healthy controls. IgG4 antibody response in bee venom sensitive individuals has been studied and it has been suggested that IgG4 may act as blocking antibody. However in studies of BV sensitive individuals by applicants a clear cut correlation between bee venom specific IgG4 and sensitivity or protection could not be found. Among bee sting sensitive patients, severe or mild systemic reactions occurred in a small percentage of individuals who had low or moderate amounts of IgG4 antibodies to BV, while only one out of 14 individuals who had high levels of IgG4 had a mild systemic reaction to BV and the remainder showed only local reactivity. This may be the case because cells producing IgG4 are mainly found in the mucosal associated lymphoid tissue. Venom specific IgE antibody levels may initially rise but usually fall with IT. Venom specific IgG antibody levels may initially increase but as immunotherapy proceeds IgG levels plateau or even drop in the face of continued protection. Failure of protection even in the presence of adequate levels of specific IgG antibodies as well as protection in the absence of elevation in specific IgG antibodies have been observed. It has been shown that in some cases non-IgE antibodies to allergen(s) may not inhibit the binding of IgE to the allergen(s). Therefore, there may be a discrepancy in the notion that venom specific 'blocking' IgG antibody competition for the venom antigen with IgE antibodies is a sole factor in affording protection with bee venom immunotherapy. Taken together these findings point to other factor(s) which may be involved in the modulation of the immune response. Anti-idiotypic antibodies can modulate immune responses and may well be a major influence in protection afforded by IT.

Classically the individual antigenic specificities of antibodies or antigen specific cell receptors are referred to as idiotypes. The individual immunogenic structures in the variable region of homogeneous antibodies or antigen-specific cell receptors are called idiotypes. Antibodies to idiotypes are referred to as anti-idiotypes. The existence of idiotypes and anti-idiotypes, both as soluble immunoglobulins in the serum and as lymphocyte receptors involved in a complex network of interactions that regulate immune response has been demonstrated by many observations. In the strictest sense, every idiotype within the repertoire of possible idiotypes is in turn a self-antigen for complementary anti-idiotype. Hence the mechanisms regulating autologous idiotype should be applicable to any anti-idiotype.

Intentionally induced idiotype suppression by parenteral administration of anti-idiotypic antibodies and the natural occurrence of anti-idiotypic antibodies following immunization with conventional antigens represent clear examples of the potential inhibitory influence of anti-idiotypic antibodies on the immune response. In other instances, it can be shown that anti-idiotypic antibodies enhance the immune response. It seems that the effects produced depend on the idiotypic specificities expressed by the receptors of B cells and by both helper and suppressor T cells involved in the immune response triggered by a particular antigen.

Extensive studies of the antibody response to Benzylpenicilloyl (BPO) and Phosphorylcholine (PC) have been carried out and it has been concluded that idiotypes present on IgE, IgG, IgA and IgM antibodies to these antigens are identical or very similar. Using mouse models for the production of IgE antibodies, it has been shown that anti-BPO antibodies of IgE class could be actively suppressed in mice producing anti-idiotypic antibodies to anti-BPO which could also suppress anti-BPO IgE antibodies by passive transfer of anti-BPO anti-idiotypic antibodies. Moreover, anti-idiotypic antibody production has been shown in the course of a normal immune response. IgG auto-anti-idiotypic antibodies to anti-Rye 1 have been isolated from a single Rye-sensitive patient. These anti-idiotypic antibodies blocked the reaction of IgE and IgG anti-Rye 1 to Rye antigen. The relationship of these antibodies to immunotherapy could not be established because the patient from whom the serum was obtained was on immunotherapy for several years before the serum specimen could be collected. In addition, the role of anti-idiotypic antibodies in the modulation of immune response in this instance could not be established because longitudinal studies were not carried out. Auto-anti-idiotypic antibodies have been detected in normal individuals after booster immunization with tetanus toxoid. These antibodies have been shown to inhibit the synthesis of anti-tetanus toxoid antibodies by peripheral blood lymphocytes of the individuals in vitro. Rabbit anti-idiotypic antibodies against human anti-tetanus toxoid were shown to inhibit in vitro IgE anti-tetanus toxoid synthesis by lymphocytes from individuals producing anti-tetanus toxoid antibodies. The possibility that idiotypic anti-idiotypic interactions play a role in human T cell response to antigen was also studied in this system. The study showed that rabbit anti-idiotypic antibodies to anti-tetanus toxoid were capable of generating antigen specific suppressor cells when T cells from sensitized individuals were incubated with anti-idiotypic antibodies.

Little is known about the production of auto-anti-idiotypic antibodies in allergic patients during immunotherapy. We hypothesize that anti-idiotypic antibodies reactive against bee venom specific antibodies are produced in multiple stung beekeepers and during bee venom immunotherapy. These antibodies (a) suppress bee venom specific IgE antibody responses, (b) bind to preformed bee venom specific IgE and effectively compete with available bee venom constituents.

OBJECT OF INVENTION

It is an object of the present invention to provide anti-idiotypic antibodies to anti-bee venom.

It is another object of the present invention to provide a method for determining the sensitivity of selected patients to bee venom.

It is yet another object to provide a diagnostic kit using monoclonal antibodies.

BRIEF STATEMENT OF INVENTION

Thus, by one aspect of this invention there is provided a method for determining protection against an anaphylactic reaction of an individual exposed to hymenoptera stings comprising:

measuring anti-idiotypic antibodies to anti-hymenoptera venom present in the serum of said individual.

By another aspect of this invention there is provided an anti-idiotypic antibody to anti-bee venom.

By yet another aspect of this invention there is provided a monoclonal anti-bee venom antibody reactive to anti-bee venom anti-idiotype. And by further aspect there is provided a diagnostic kit for determining hymenoptera venom anti-idiotypic antibody in serum, comprising:

(a) a solid base support have immobilized thereon a specific mouse monoclonal antibody directed against said anti-idiotypic antibody;

(b) a reagent containing an enzyme conjugated to a polyclonal antibody directed against human immunoglobulin; and (c) a colour developer solution containing a substrate for said enzyme.

DETAILED DESCRIPTION OF PREFERRED EMBODIMENTS

Isolation and purification of an active bee venom constituent to which patient serum antibodies react.

Figure 1:
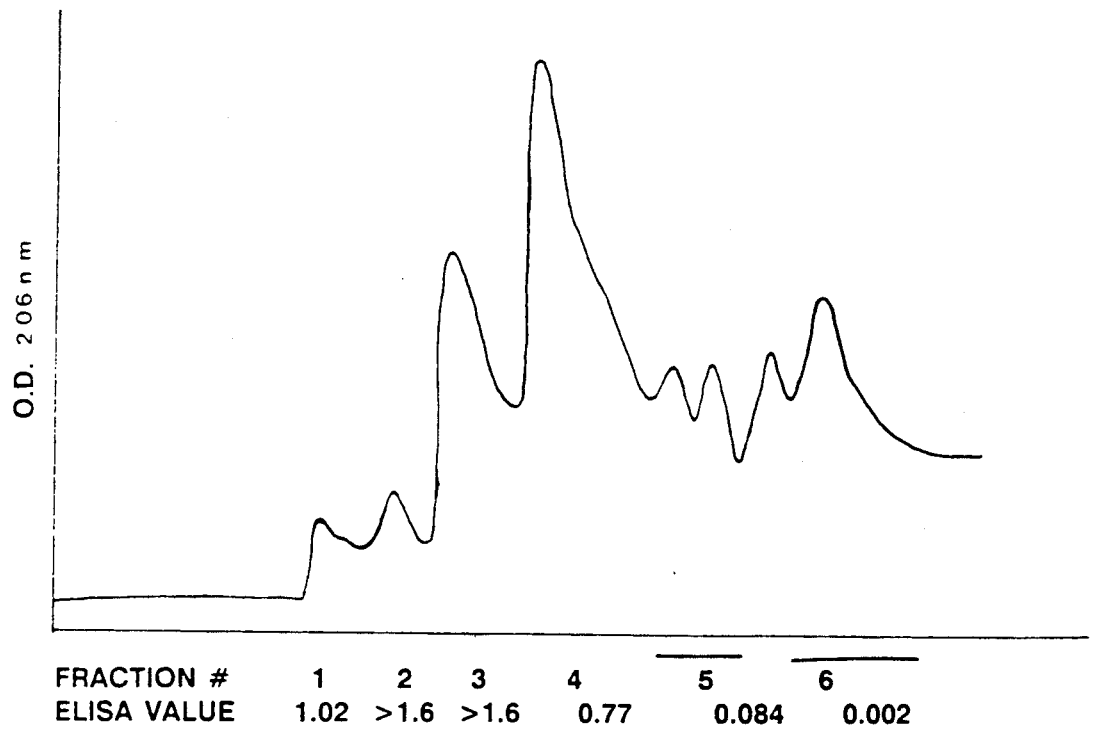
FIG. 1 is a chromatograph showing fractionation of bee venom on SEPHADEX G-75 column.

For the affinity purification of bee venom specific antibodies and for the detection of anti-bee venom, commercially obtained bee venom was fractionated on SEPHADEX G-75 column. SEPHADEX and SEPHAROSE are trademarks of Pharmacia Fine Chemicals Inc. for a series of gel filtration media. ELISA values of known bee venom positive serum tested in a micro ELISA assay using plates coated with 10 ug/ml from each peak are shown under each peak. It can be seen from FIG. 1 that the first three protein peaks have most of the antigenic activity. The largest protein peak has very little activity and subsequent peaks have no antigenic activity. These were pooled together, aliquoted and kept frozen. For affinity purification of anti-bee venom, purified bee venom was coupled to cyanogen bromide activated SEPHAROSE. Gamma globulins from two strongly positive sera were prepared by ammonium sulphate precipitation method, and applied to bee venom SEPHAROSE column. Non-bound proteins were removed by extensive washing of the column with phosphate buffered saline and bound anti-bee venom antibodies were eluted using glycine HCl buffer pH 3.5 containing 0.5M sodium chloride. Eluted antibodies were dialyzed against phosphate buffered saline, labelled with biotin and passed over a column of normal human serum coupled to SEPHAROSE to remove non-specific activity from this probe. In some experiments, an F(ab')2 fragment prepared from affinity purified anti-bee venom, labelled with biotin and adsorbed against normal human serum as described was used to detect anti-idiotypic antibodies to anti-bee venom.

Using this active bee venom component, anti-BV antibodies from a patient's serum were obtained by affinity separation on an affinity column of BV conjugated to cyanogen bromide activated SEPHAROSE beads. The affinity purified anti-BV antibody was further adsorbed on normal human non-specific IgG immunoglobulin prepared from strongly positive sera by ammonium sulphate precipitation in order to remove Fc binding rheumatoid factors. In addition, all serum samples were tested for the presence of rheumatoid factors and found to be negative.

Figure 2:
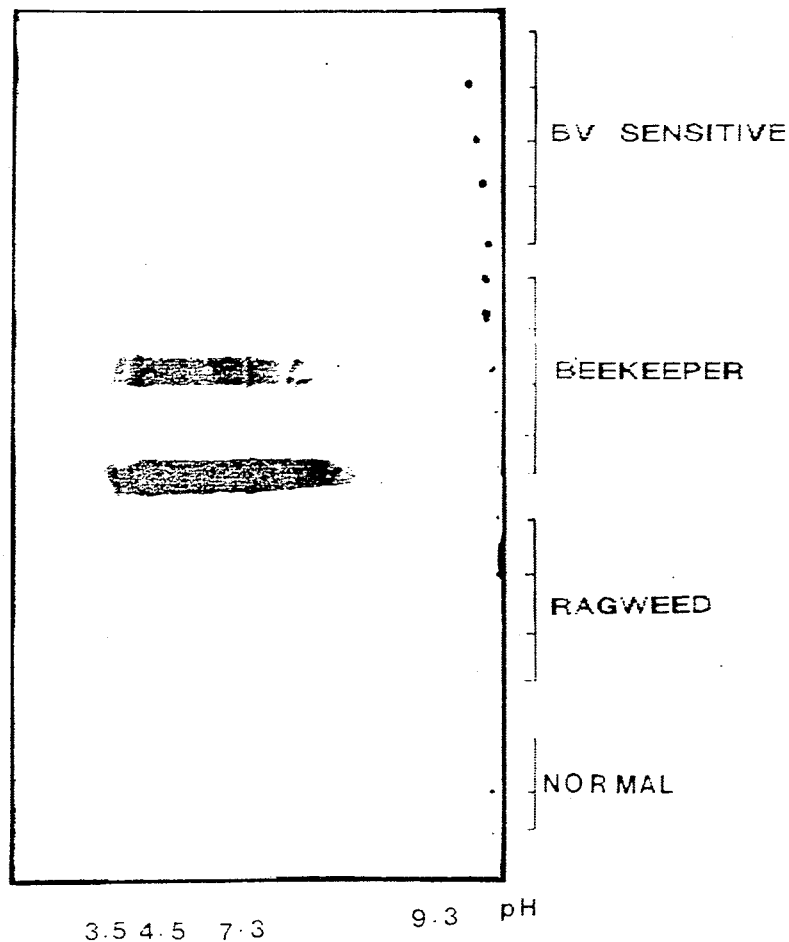
FIG. 2 is a chromatograph showing anti-bee venom activity in sera from BV sensitive persons, non-reactive beekeepers and ragweed sensitive persons.

After biotinylation an F(ab')2 fragment prepared from the affinity purified anti-BV was used as a probe for anti-idiotype antibodies to anti-bee venom in patient's serum after isoelectric focusing across a broad pH gradient on agarose gels and capillary blotting onto nitrocellulose paper. FIG. 2 shows anti-bee venom activity in sera obtained from bee venom sensitive persons, non-reactive beekeepers and ragweed sensitive individuals with no known exposure to bee venom. It can be seen that beekeepers produce large amounts of anti-bee venom antibodies which can be seen as intensely staining bands. Some bee venom sensitive individuals can also be seen. What is also seen is the heterogeneity of the anti-bee venom response in beekeepers as evidenced by the stained bands in the entire pH range. After extensive washing and blocking with Tween ®-20 (5-bromo-4 chloro-3 indolyl phosphate), alkaline phosphatase-conjugated streptavidin was added and the reaction developed for colour using BCIP (poly oxyethylene sorbitan monolaurate) and NBT (Nitroblue tetrazdium) (Bio-Rad). In addition, protein A absorption of anti-idiotype positive serum removed their reactivity with the anti-BV probe. Since protein A binds mainly IgG from human sera, this is further evidence of anti-idiotypic antibodies in these sera.

The following table summarizes the results.

A binds mainly IgG from human serum, this is further evidence that it is anti-idiotypic antibodies in these sera which are being detected.

Figure 5:
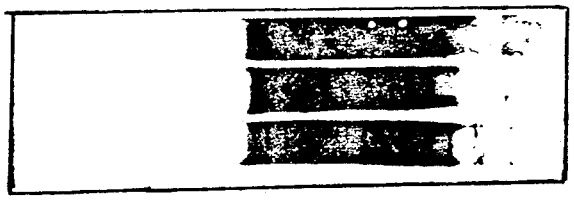
FIG. 5 is a chromatograph illustrating the development of anti-idiotypic antibody to anti BV with increasing immunotherapy.

These results illustrate that a high percentage of non-reactive beekeepers test positive for anti-idiotypic antibodies against anti-BV relative to ragweed sensitive controls with no known exposure to bee venom. None of the bee sting sensitive patients had detectable anti-idiotypic antibodies but 67% of the patients on bee venom immunotherapy have detectable anti-idiotypic antibodies. It should also be noted that prior to immunotherapy, none of these patient's serum had detectable amounts of anti-idiotypic antibodies. FIG. 5 shows that prior to venom therapy there were no anti-idiotypic antibodies to anti-bee venom, but anti-idiotypic antibodies to anti-bee venom develop in the serum specimens of patients on venom therapy. Furthermore the intensity of staining for anti-idiotypic antibody to anti-bee venom seems to increase with longer immunotherapy.

Isolation of Anti-idiotypic Antibodies Against Anti-BV

Serum from bee venom sensitive patients for high titer anti-BV antibody was screened using the ELISA procedure. A limit of 3 high titer antibody sera from each of the patients was selected. Here, the advantage of utilizing serum IgG F(ab')2 anti-BV preparations offers a better likelihood of identifying cross reactive public idiotypes, amplifying the screening procedure for anti-idiotypic antibodies.

F(ab')2 fragment of anti-BV produced is described above was coupled to cyanogen bromide-activated Sepharose. This immunoabsorbent was used to isolate anti-idiotypic antibodies to anti-BV as follows. Serum specimens containing large amounts of anti-idiotypic antibodies were used to prepare gamma globulins by 50% ammonium sulphate precipitation. The gamma globulin preparation was passed over BV-

TABLE 1

| Patient status | Number of patients positive for anti-Id per total (%) | Chi-square | P-values | Yate's corr |
|---|---|---|---|---|
| Ragweed sensitive | 0/4 (0) | | | |
| Bee sting sensitive | 0/5 (0) | 1.0000 | N.S. | |
| Beekeepers non-reactive | 13/15 (87) | 10.9778 | 0.00092 | 0.0067 |
| Bee venom immunotherapy | 2/3 (67) | 3.7333 | 0.05334 | 0.2771 |

Figure 3:
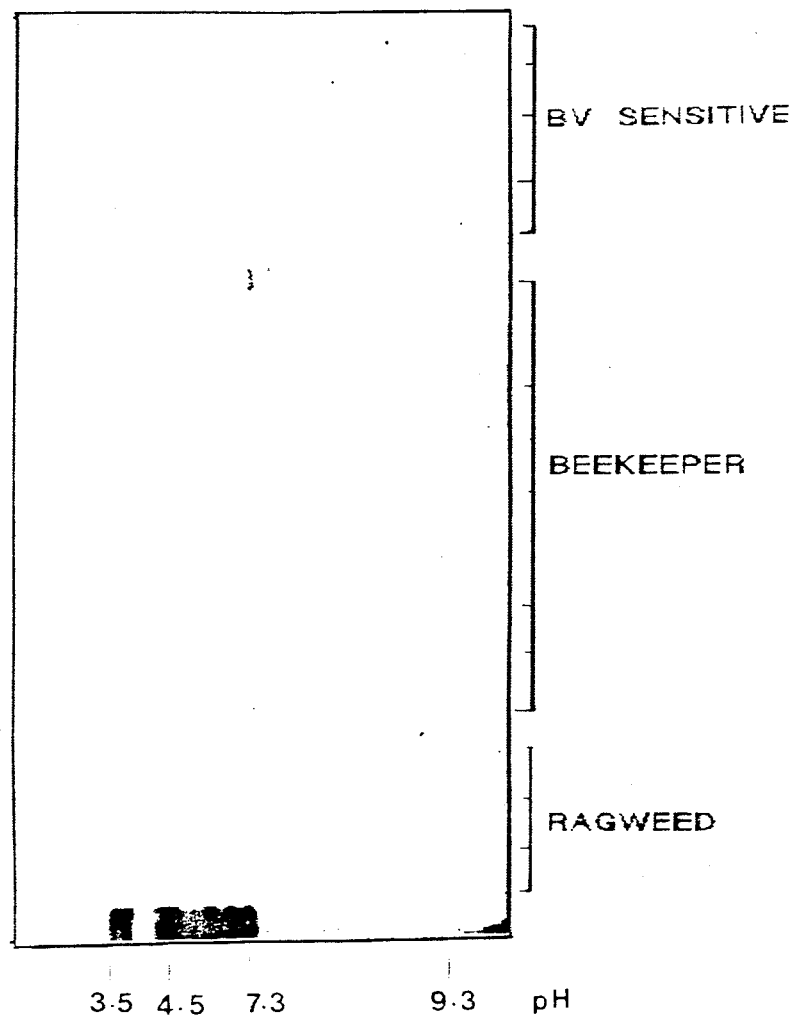
FIG. 3 is a chromatograph showing anti-bee venom anti-idiotypic antibodies in sera from non-reactive beekeepers.

FIG. 3 shows the anti-bee venom anti-idiotypic antibodies in sera obtained from non reactive beekeepers. It can be seen that while sera from bee sting sensitive individuals and from ragweed sensitive individuals are completely negative, sera from beekeepers are positive. Some beekeepers express more anti-idiotypic antibody than others. This may reflect the frequency or number of stings received by individual beekeepers. The last lane in FIG. 3 contained biotin labelled pI markers which were run simultaneously to identify the pH gradient. Since affinity purified anti-bee venom was used as a probe it is conceivable though unlikely that it is circulating bee venom in the serum specimen which is being detected. In order to identify the nature of the reacting substance in the serum, serum specimens from two beekeepers whose sera gave strong positive reactions were selected. An aliquot of each serum was then adsorbed on protein A SEPHAROSE, non-bound proteins were collected and electrofocused simultaneously with the serum.

Figure 4:
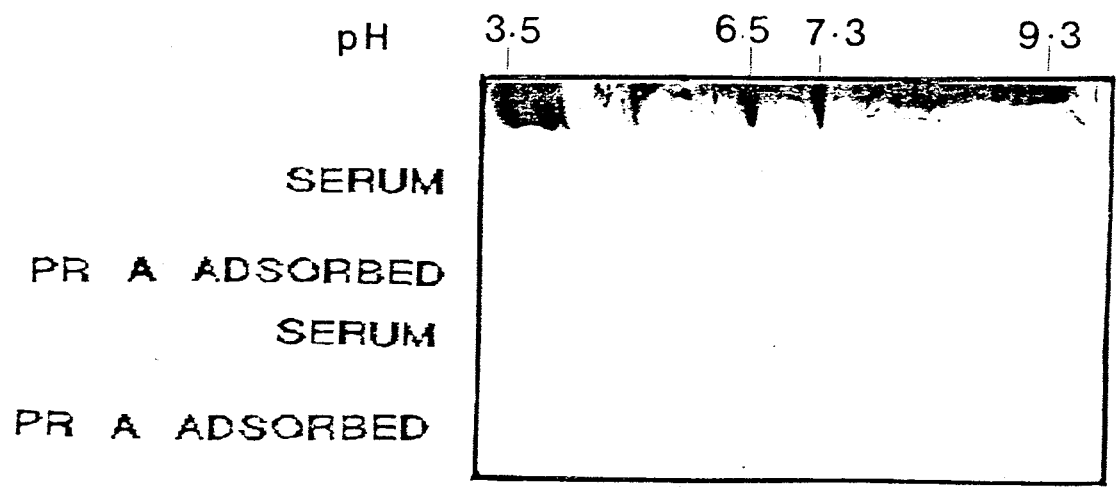
FIG. 4 is a chromatograph showing protein A adsorption of the positive serum.

FIG. 4 shows that protein A adsorption of the positive serum removed most of its reactivity. Since protein SEPHAROSE to remove anti-BV antibodies. The unbound proteins were removed by extensive washing with buffer solution and bound anti-idiotypic antibodies were eluted with 0.1M acetic acid, 0.5M NaCl pH 3.5 or Glycine HCl buffer pH 3.5. The isolated antibodies were dialysed against PBS, concentrated, and sterilized by millipore filtration. Following elution, purified BV anti-idiotypic antibodies were tested for specific reactivity to autologous idiotype (anti-BV), different donor idiotypes, non-reactive F(ab')2 to BV, and an irrelevant idiotype (anti-ragweed). Various dilutions of these antibodies were then used to detect their modulating effects on IgE anti-BV synthesis in vitro.

Modulation of IgE anti-BV antibody production by anti-idiotypic antibodies

Aliquots of cells from each subject were cultured in the presence and absence of anti-idiotypic antibodies to anti-BV in addition to antigen. Cells from control groups sensitive to unrelated antigens or normal subjects were similarly cultured. A comparison between the amount of IgE anti-BV was made to determine the modulating effects of anti-idiotypic antibodies on the IgE anti-BV response of these cells, using the ELISPOT procedure. BV coated microtiter PVC plates were layered with isolated peripheral blood lymphocytes and incubated for 2 hours. The cells were then washed off and the wells coated with alkaline phosphatase conjugated goat anti-human IgE specific antibody. The wells were then covered with agarose containing substrate for colour development. The ELISPOT method is effective. Specificity of the modulating effects was determined by the influence of anti-BV anti-idiotype antibodies on IgE anti-ragweed antibody production.

Isolation of Antibodies to Bee Venom (BV)

Blood was obtained from patients with a history of honey bee sting sensitivity after informed consent. Serum was prepared by clotting the blood and gamma globulins prepared by 50% ammonium sulphate precipitation. After dialysis against appropriate buffer anti-bee venom antibodies were isolated from the gamma globulin preparation by affinity chromatography on a column using BV-SEPHAROSE. The isolated antibodies were passed over a column of Sepharose conjugated normal human gamma globulin to remove Rheumatoid Factor (RF) activity. RF activity was checked before digestion and anti-BV antibodies ware digested with pepsin. The F(ab')2 fragment prepared was biotinylated by a standard method.

Monoclonal anti-BV antibody generation

Mice were immunized with BV intraperitoneally. Three weeks later mice were given a booster injection and the serum tested for antibodies against the protein using a sensitive nitrocellulose ELISA procedure which can be used for small quantities of protein applications. A mouse with high antibody titer was selected for the generation of monoclonal antibodies.

Hyperimmune spleen cells were fused to the murine fusion partner SP2/0 Ag14 (non-immunoglobulin producer) using standard hybridoma technologies. Here, individual spleen cells were fused in polyethylene glycol (PEG) with SP2/0 tumor cells which are selected for purine enzyme deficiency and for their inability to secrete Ig. The resulting fused cells (hybridomas) are cloned in micro-well plates in HAT (hypoxanthine, aminopterin, thymidine) medium which kills off the perfusion partners, at high dilution such that, on an average, each well will contain less than one hybridoma cell. Thus, each hybridoma per well is clonally expanded and the supernatants screened for monoclonal antibody production using BV coated nitrocellulose ELISA test. All positive hybridomas were grown as ascites in nude mice after they had been cloned at least three times. Isotyping of the selected monoclonal antibodies was done using an ELISA-based isotyping kit.

Development of a diagnostic kit using monoclonal antibodies

A qualitative as well as a quantitative, non-instrumental, test-strip enzyme immunoassay for BV anti-idiotypic antibody in serum, which is based on the activity of a tracer has been produced. The total BV anti-idiotypic antibody enzyme immunoassay kit is a two sites method using two mouse monoclonal antibodies directed against two different parts of the protein in question. The first monoclonal antibody is fixed on a nitrocellulose disk positioned at the end of plastic strip, the second antibody is labelled with an enzyme (e.g. alkaline phosphatase).

Three important components in the assay are (a) a dry nitrocellulose disk attached to a plastic strip to which has been immobilized specific monoclonal antibody directed against the antibody of interest; (b) an enzyme reagent containing alkaline phosphatase conjugate of a second antibody directed against a different site on the protein of interest; (c) a colour-developer solution containing substrate for the enzyme.

Sample specimen from a patient is added to a container. The end of the antibody strip is then inserted into the patient's sample and let to incubate at ambient temperature for 30 minutes (with agitation) or 2 hours (without agitation). The strip is then removed from the sample, and washed in a buffer solution. The strip is inserted in a tracer (antibody 2 conjugated with an enzyme) and let incubate for 1 hour (with agitation) or overnight (without agitation). Again the strip is washed in a buffer solution after which it is inserted into a colour-developer solution containing the substrate for the enzyme. A third reagent consisting of BCIP and NBT (Bio-Rad) is used to form an insoluble colour deposit on the nitrocellulose disk. When the strip is immersed in Reagent 3, an insoluble blue product forms on the portion of the nitrocellulose disk. The colour change results from coupled enzyme reactions involving the enzyme, alkaline phosphatase and its substrate. Colour intensity is converted to quantity of protein present in the sample from a result table of known amounts of protein as well as by negative controls.

Result-reading Study

The test result is obtained by visually measuring the intensity of the colour on the disk against a scale on a plastic cassette and then using a result table to convert the measurement to a sample concentration. This feature eliminates the need for an instrument to measure the end point.

We claim:

1. A method for determining protection against an anaphylactic reaction of an individual exposed to hymenoptera stings comprising:
   contacting a serum sample from said individual with a labeled antibody specific to hymenoptera venom so as to bind any anti-hymenoptera venom anti-idiotypic antibodies present therein; and
   detecting the binding of said anti-hymenoptera venom anti-idiotypic antibodies present in the serum of said individual as a measure of protection against anaphylactic reaction.

2. A method as claimed in claim 1 wherein said hymenoptera are bees.

3. A method as claimed in claim 2 wherein said determining is performed by isoelectric focussing in agarose gels, the contacting step is performed using a biotin-labeled probe to detect anti-bee venom anti-idiotypic antibodies, and the detecting step is performed using alkaline phosphatase conjugated to streptavidin so as to produce a colored product as an indication of the presence of anti-bee venom anti-idiotypic antibodies.

4. A method for determining protection against an anaphylactic reaction of an individual exposed to hymenoptera stings comprising:
   raising a mouse monoclonal antibody directed against hymenoptera venom;
   raising a polyclonal specific anti-human immunoglobulin antibody and labeling said polyclonal antibody with an enzyme;
   fixing said monoclonal antibody on a solid phase support;
   incubating a patient serum sample with said support containing said monoclonal antibody so as to bind any anti-idiotypic antibodies contained in said serum sample;

incubating said incubated support with said labeled polyclonal specific anti-human immunoglobulin antibody;

immersing and incubating said incubated support in a color developer solution containing a substrate for said enzyme so as to develop a color change indicative of said anti-idiotypic antibody; and measuring said anti-idiotypic antibody as a function of said color change.

5. A method as claimed in claim 4 wherein said hymenoptera are bees.

* * * * *